(12) United States Patent
Cziryak et al.

(10) Patent No.: US 11,850,298 B2
(45) Date of Patent: Dec. 26, 2023

(54) ANTI-AGING COMPOSITIONS AND SKIN MASKS CONTAINING ANTI-AGING COMPOSITIONS

(71) Applicant: L'OREAL, Paris (FR)

(72) Inventors: Paula Cziryak, Eatontown, NJ (US); Valérie Robert, Scotch Plains, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/915,734

(22) Filed: Jun. 29, 2020

(65) Prior Publication Data

US 2020/0405611 A1   Dec. 31, 2020

Related U.S. Application Data

(60) Provisional application No. 62/868,558, filed on Jun. 28, 2019.

(51) Int. Cl.

| A61K 8/64 | (2006.01) |
|---|---|
| A61K 8/02 | (2006.01) |
| A61K 8/36 | (2006.01) |
| A61K 8/60 | (2006.01) |
| A61K 8/73 | (2006.01) |
| A61K 8/81 | (2006.01) |
| A61Q 19/08 | (2006.01) |

(52) U.S. Cl.
CPC .............. *A61K 8/64* (2013.01); *A61K 8/0212* (2013.01); *A61K 8/361* (2013.01); *A61K 8/606* (2013.01); *A61K 8/73* (2013.01); *A61K 8/731* (2013.01); *A61K 8/735* (2013.01); *A61K 8/8176* (2013.01); *A61Q 19/08* (2013.01)

(58) Field of Classification Search
CPC ...................................................... A61Q 19/08
See application file for complete search history.

(56) References Cited

U.S. PATENT DOCUMENTS

| 6,379,702 B1 | 4/2002 | Lorenz et al. | |
|---|---|---|---|
| 9,067,967 B2 * | 6/2015 | García Antón | A61K 38/00 |
| 2008/0107679 A1 * | 5/2008 | Dilallo | A61K 36/04 |
| | | | 424/195.17 |
| 2009/0041815 A1 | 2/2009 | Legendre | |
| 2010/0203108 A1 | 8/2010 | Terashi et al. | |
| 2013/0244977 A1 * | 9/2013 | Lee | A61K 8/731 |
| | | | 514/57 |
| 2016/0213600 A1 * | 7/2016 | Klostermann | A61K 8/895 |
| 2016/0279162 A1 * | 9/2016 | Richard | A61K 31/728 |

FOREIGN PATENT DOCUMENTS

| CN | 104736136 A | 6/2015 | | |
|---|---|---|---|---|
| CN | 107137263 A | 9/2017 | | |
| EP | 3047845 A1 | 7/2016 | | |
| FR | 2893503 B1 | 4/2008 | | |
| FR | 2907006 A1 | 4/2008 | | |
| FR | 2918275 B1 | 1/2009 | | |
| FR | 3080534 A1 * | 11/2019 | ............. | A61Q 19/08 |
| JP | 2010207571 A | 9/2010 | | |
| KR | 20150078137 A * | 7/2015 | ............... | A61K 8/64 |
| KR | 101831756 B1 * | 2/2018 | ........... | A61K 8/9789 |
| KR | 100866609 B1 * | 11/2018 | ............... | A61K 8/64 |

OTHER PUBLICATIONS

Pickart et al, GHK Peptide as a Natural Modulator of Multiple Cellular Pathways in Skin Regeneration, Skin Regeneration, Repair, and Reconstruction, vol. 2015, publication date Jul. 7, 2015 (Year: 2015).*
Mintel Lifting Mask (Database GNPD Mintel, Jan. 4, 2019) (Year: 2019).*
Mintel Triangle of Light Eye Mask (Database GNPD Mintel, Jul. 13, 2015) (Year: 2015).*
Specialchem, Argireline (Acetyl Hexapeptide-3) Powder, last edited Nov. 5, 2020 (Year: 2020).*
Proksch et al, Topical use of dexpanthenol: a 70th anniversary article, Journal of Dermatological Treatment, vol. 28, 2017—Issue 8, publication date May 14, 2017 (Year: 2017).*
KR100866609B1 (Google english translation, downloaded in Dec. 2020) (Year: 2020).*
FR3080534A1 (Google English translation, downloaded in Dec. 2020) (Year: 2020).*
MB Loves Skin Care, Breaking Down the Ordinary—The Mighty Ten Working Together, publication date: Jan. 24, 2018 (Year: 2018).*
KR101831756b1, Google English Translation, Downloaded in Nov. 2021 (Year: 2021).*
KR20150078137A, Korean Intellectual Property Office translation document of KR20130167258 which is the application document of KR20150078137A, downloaded in Oct. 2022 (Year: 2022).*
PCT Notification of Transmittal of the International Search Report and the Written Opinion of the International Searching Authority, issued to Application No. PCT/US2020/040166 dated Sep. 17, 2020.
Mintel, "Lifting Mask", XP055727600, database accession No. 6237543, Jan. 4, 2019, www.gnpd.com.
Mintel, "Triangle of Light Eye Mask", XP05572824, database accession No. 3220131, Jul. 13, 2015, www.gnpd.com.

* cited by examiner

*Primary Examiner* — Mark V Stevens
*Assistant Examiner* — Alparslan Asan
(74) *Attorney, Agent, or Firm* — McNees Wallace & Nurick LLC

(57) ABSTRACT

In some embodiments, an anti-aging composition includes hyaluronic acid, at least one anti-aging peptide, at least one skin penetration enhancer, and water. In some embodiments, an anti-aging composition includes hyaluronic acid, at least one anti-aging peptide, at least one tensing polymer, and water. An anti-aging product includes a skin mask patch and an anti-aging composition loaded into the skin mask patch. A method of forming an anti-aging product includes forming an anti-aging composition and loading the anti-aging composition into a skin mask patch.

19 Claims, No Drawings

ANTI-AGING COMPOSITIONS AND SKIN MASKS CONTAINING ANTI-AGING COMPOSITIONS

CROSS-REFERENCE TO RELATED APPLICATIONS

This patent application claims the benefit of priority under 35 U.S.C. § 119(e) to U.S. Provisional Patent Application Ser. No. 62/868,558, filed on Jun. 28, 2019, entitled "ANTI-AGING COMPOSITIONS AND SKIN MASKS CONTAINING ANTI-AGING COMPOSITIONS," the disclosure of which is incorporated herein by reference as if fully rewritten herein.

FIELD OF THE INVENTION

The invention relates to cosmetic compositions, masks containing such cosmetic compositions, and methods including such cosmetic formulations. More specifically, the invention relates to anti-aging compositions, skin masks containing anti-aging compositions, and methods including anti-aging compositions.

BACKGROUND OF THE INVENTION

Anti-aging compositions, such as, for example, reduction of wrinkles in skin may be applied by way of either a cream or a skin mask, but twice daily application is typically required for positive results within a month time period. Such a high frequency of application may be inconvenient for the user and may lead to other skin issues. Commonly-treated wrinkles may include crow's feet, nasolabial wrinkles, and glabella wrinkles.

Skin masks, such as, for example, full-face masks, are typically shaped to fit a specific way such that any pre-loaded anti-aging compositions are applied only to specific skin locations.

There is a need for a formulation that overcomes one or more of the aforementioned drawbacks associated with formulations and products that provide a reduction of wrinkles.

BRIEF SUMMARY OF THE INVENTION

The summary is provided to introduce a selection of concepts in a simplified form that are further described below in the detailed description of the invention. This summary is not intended to identify key features of the claimed subject matter, nor is it intended to be used as an aid in determining the scope of the claimed subject matter.

The cosmetic compositions hereof are characterized, in various embodiments, as including hyaluronic acid, at least one anti-aging peptide, at least one skin penetration enhancer and/or at least one tensing polymer, and water.

In some embodiments, an anti-aging composition includes hyaluronic acid, at least one anti-aging peptide, at least one skin penetration enhancer, and water.

In some embodiments, an anti-aging composition includes hyaluronic acid, at least one anti-aging peptide, at least one tensing polymer, and water.

In some embodiments, an anti-aging product includes a skin mask patch and an anti-aging composition loaded into the skin mask patch.

In some embodiments, a method of forming an anti-aging product includes forming an anti-aging composition and loading the anti-aging composition into a skin mask patch, wherein the anti-aging composition includes hyaluronic acid, at least one anti-aging peptide, at least one tensing polymer, and water.

The methods hereof are characterized, in various embodiments, as providing a reduction in the appearance of wrinkles, such as, for example, after a month of application of an anti-aging product with a frequency, for example, of three times per week for a time period, for example, of 30 minutes per application.

Other features and advantages of the present invention will be apparent from the following more detailed description, by way of example, the principles of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

DETAILED DESCRIPTION OF THE INVENTION

According to the disclosure, a cosmetic composition and a method are provided that include an anti-aging composition.

The anti-aging composition provides the surprising and unexpected benefit of a statistically-significant reduction in wrinkles based on clinical grading by experts and self-assessment by users after a total of only twelve thirty-minute applications, three days per week.

The anti-aging composition may be any water-based line-reducing or wrinkle-reducing composition. In some embodiments, the anti-aging composition includes hyaluronic acid, at least one anti-aging peptide, at least one skin penetration enhancer, and water. In some embodiments, the anti-aging composition includes hyaluronic acid, at least one anti-aging peptide, at least one tensing polymer, and water.

In some embodiments, the anti-aging composition is part of an anti-aging product. In some embodiments, the anti-aging composition is loaded into a skin mask to form the anti-aging product. In some embodiments, the skin mask is a skin mask patch.

The skin mask may be any material capable of holding and releasing the anti-aging composition and adhering to the skin. In some embodiments, the skin mask includes a hydrogel, into which the anti-aging composition is loaded. In some embodiments, the skin mask includes biocellulose, into which the anti-aging composition is loaded.

The skin mask may be any shape capable of contacting the skin with the lines or wrinkles to be reduced and releasing the anti-aging composition to the skin. In some embodiments, the skin mask has a triangular shape with the three sides significantly greater than the thickness of the skin mask. The triangular shape may be any triangular shape, including, but not limited to, equilateral, isosceles, scalene, right, obtuse, acute, or right isosceles. The triangular shape may have any dimensions. In some embodiments, the triangular dimensions are about 1.5 inches by about 2 inches by about 1.5 inches.

A triangular shape of a skin mask permits many configurations on different parts of the body, such as, for example, the hands, the feet, and the face, such as, for example, around the eyes, forehead, and nasolabial areas.

Hyaluronic Acid

In accordance with the disclosure, provided are anti-aging compositions that include hyaluronic acid. In exemplary embodiments, the hyaluronic acid aids in smoothing and plumping the skin. In some embodiments, the hyaluronic acid is in the form of hydrolyzed hyaluronic acid. In some embodiments, the hyaluronic acid is in the form of sodium hyaluronate.

The hyaluronic acid may be provided in the anti-aging composition in any appropriate amount. More particularly, the hyaluronic acid may be present in the anti-aging composition at a concentration, by weight, based on the total weight of the anti-aging composition, of about 0.01% to about 1%, alternatively from about 0.05% to about 0.5%, alternatively from about 0.07% to about 0.2%, alternatively from about 0.08% to about 0.15%, or any value, range, or sub-range therebetween. Thus, the hyaluronic acid may be present in an amount from about 0.01%, 0.05%, 0.1%, 0.2%, 0.3%, 0.4%, 0.5%, 0.6%, 0.7%, 0.8%, 0.9%, to about 1%.

Anti-Aging Peptides

In accordance with the disclosure, provided are anti-aging compositions that include one or more anti-aging peptides. In exemplary embodiments, the anti-aging peptides provide long-term biological wrinkle or line efficacy. Anti-aging peptides may include, but are not limited to, one or more acetyl hexapeptides, acetyl hexapeptide-8, one or more acetyl tetrapeptides, acetyl tetrapeptide-9, and combinations thereof.

In other embodiments, the composition may include any one or more of acetyl hexapeptides (e.g., acetyl hexapeptide-3, -37, -38, and -51) and other acetyl tetrapeptides (e.g., acetyl tetrapeptide-2, -3, -5, -7, -8, -9, -11, and -15), and combinations thereof.

The anti-aging peptides may be provided in the anti-aging composition in any appropriate amount. More particularly, the anti-aging peptides may be present in the anti-aging composition at a total concentration, by weight, based on the total weight of the anti-aging composition, of about 0.001% to about 0.1%, alternatively from about 0.001% to about 0.01%, alternatively from about 0.001% to about 0.005%, alternatively from about 0.0012% to about 0.004%, or any value, range, or sub-range therebetween. Thus, the anti-aging peptides may be present in an amount from about 0.001%, 0.005%, 0.01%, 0.02%, 0.03%, 0.04%, 0.05%, 0.06%, 0.07%, 0.08%, 0.09%, to about 0.1%.

Skin Penetration Enhancers

In accordance with the disclosure, provided are anti-aging compositions that include one or more skin penetration enhancers. In exemplary embodiments, the skin penetration enhancers aid in penetration of the anti-aging composition into the skin. Skin penetration enhancers may include, but are not limited to, oleic acid.

In other embodiments, the composition may include any one or more of skin penetration enhancers selected from capric acid, lauric acid, myristic acid, palmitic acid, stearic acid, palmitoleic acid, linoleic acid, linolenic acid, lignoceric acid, resinoleic acid, arachidonic acid, and combinations thereof.

The skin penetration enhancers may be provided in the anti-aging composition in any appropriate amount. More particularly, the skin penetration enhancers may be present in the anti-aging composition at a total concentration, by weight, based on the total weight of the anti-aging composition, of about 0.01% to about 0.5%, alternatively from about 0.05% to about 0.3%, alternatively from about 0.08% to about 0.2%, alternatively from about 0.12% to about 0.18%, or any value, range, or sub-range therebetween. Thus, the skin penetration enhancers may be present in an amount from about 0.01%, 0.02%, 0.03%, 0.04%, 0.05%, 0.06%, 0.08%, 0.1%, 0.2%, 0.3%, 0.4%, to about 0.5%.

Tensing Polymers

In accordance with the disclosure, provided are anti-aging compositions that include one or more tensing polymers. In exemplary embodiments, the tensing polymers provide rapid or immediate tensing of the skin. Tensing polymers may include, but are not limited to, pullulan, polyvinylpyrrolidone (PVP), and combinations thereof.

In other embodiments, the composition may include any one or more of bio-cellulosic tensing polymers selected from cellulose, microbial cellulose, bacterial cellulose, bacterial cellulose in spherical form, cellulose pulp, cellulose derivatives, carboxymethyl cellulose, methocel, chitin, chitin derivatives, chitosan, starch, starch derivatives, alginate, carrageenan such as kappa, iota, lambda, or other carrageenan variations, pectin, xanthan, gum arabic, konjac, gellan, locust bean, karaya, pullulan, furcellaran, and/or plant hemicelluloses such as xylan, glucuronoxylan, arabinoxylan, glucomannan, xyloglucan, and combinations thereof. In yet other embodiments, the composition may include any one or more of synthetic tensing polymers selected from polyurethane polymers and copolymers, in particular polyester-polyurethane copolymers or polyether-polyurethane copolymers; acrylic polymers and copolymers; or grafted silicone polymers; interpenetrating polymer networks (IPNs), polycondensates or star polymers, and combinations thereof. More generally, reference is made to the patent application FR2893503B1 filed Nov. 21, 2005, and to the patent application FR3080534 FILED Apr. 27, 2018 which includes additional examples of tensing polymers and tensing agents which may be employed in certain embodiments the anti-aging composition.

The tensing polymers may be provided in the anti-aging composition in any appropriate amount. More particularly, the tensing polymers, for example but not limited to pullulan, polyvinylpyrrolidone (PVP), and combinations thereof, may be present in the anti-aging composition at a total concentration, by weight, based on the total weight of the anti-aging composition, of about 1% to about 5%, alternatively from about 1% to about 4%, alternatively from about 1% to about 3%, alternatively from about 1.5% to about 2.5%, or any value, range, or sub-range therebetween. Thus, the tensing polymers may be present in an amount from about 1%, 1.5%, 2%, 2.5%, 3%, 3.5%, 4%, 4.5%, to about 5%.

Water

In accordance with the disclosure, the anti-aging composition is a water-based composition.

In accordance with the various embodiments, water is present in the composition at a concentration, by weight, based on the total weight of the composition, of about 30% or greater, alternatively about 40% or greater, alternatively about 50% or greater, alternatively about 85% or less, alternatively from about 30% to about 85%, alternatively from about 40% to about 80%, alternatively from about 50% to about 75%, alternatively from about 55% to about 75%, alternatively from about 60% to about 70%, or any suitable value, range, or sub-range thereof. Thus, the water may be present in an amount from about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, to about 85%.

Additives

In accordance with the disclosure, the anti-aging composition may further include at least one additive. The at least one additive may be selected to provide an anti-aging composition of a predetermined type having at least one predetermined property. The total amount of the at least one additive may be any appropriate amount, such as, for example, about 50% or less, alternatively from about 20% to about 50%, alternatively from about 25% to about 45%, alternatively from about 25% to about 40%, alternatively from about 30% to about 35%, or any suitable value, range, or sub-range thereof, by weight, based on the weight of the composition. Thus, the additives may be present in a total amount from about 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, to about 50%.

The at least one additive may include, but is not limited to, at least one active, at least one pearl pigment, at least one polymer, at least one preservative, at least one surfactant, at least one non-water solvent, or combinations thereof.

The anti-aging composition may include any number of appropriate actives as additives. Appropriate actives for the anti-aging composition may include, but are not limited to: adenosine; adenosine non-phosphate derivatives including 2'-deoxyadenosine, 2 ', 3'-isopropoylidene adenosine, toyocamycin, 1-methyladenosine; N-6-methyladenosine, adenosine N-oxide; 6-methylmercaptopurine riboside, and 6-chloropurine riboside; allantoin; bifida ferment lysate; calcium lactate; capryloyl salicylic acid; dipotassium glycyrrhizate; disodium ethylenediaminetetraacetic acid (EDTA); glycolic acid; potassium hydroxide; sodium hyaluronate; sodium hydroxide; trisodium ethylenediamine disuccinate, or combinations thereof. The total amount of the actives may be any appropriate amount, such as, for example, about 15% or less, alternatively from about 5% to about 15%, alternatively from about 10% to about 13%, by weight, based on the weight of the composition.

The anti-aging composition may include any number of appropriate pearl pigments as additives. Appropriate pearl pigments for the anti-aging composition may include, but are not limited to, composite particles including a substrate formed from mica, synthetic fluorphlogopite coated with at least one mineral pigment and at least one pearl pigment, chosen from composite particles including at least one support chosen from mica, synthetic fluorphlogopite or calcium sodium borosilicate, and completely or partially coated with one or more layers of metal oxides, in particular chosen from titanium dioxide, iron oxide, tin oxide, or combinations thereof. The total amount of the pearl pigments may be any appropriate amount, such as, for example, about 2% or less, alternatively about 1% or less, alternatively from about 0.1% to about 0.3%, by weight, based on the weight of the composition.

The anti-aging composition may include any number of appropriate polymers as additives. Appropriate polymers for the anti-aging composition may include, but are not limited to, ammonium polyacryloyldimethyl taurate, carrageenan (and) potassium chloride, ceratonia siliqua (carob) gum (and) sucrose, hydroxyethyl acrylate/sodium acryloyldimethyl taurate copolymer, polyacrylamide (and) C13-C14 isoparaffin (and) Laureth-7, xanthan gum, or combinations thereof. The total amount of the polymers may be any appropriate amount, such as, for example, about 10% or less, alternatively from about 3% to about 7%, alternatively from about 4.5% to about 6%, by weight, based on the weight of the composition.

The anti-aging composition may include any number of appropriate preservatives as additives. Appropriate preservatives for the anti-aging composition may include, but are not limited to, chlorphenesin, phenoxyethanol, sodium benzoate, or combinations thereof. The total amount of the preservatives may be any appropriate amount, such as, for example, about 1% or less, alternatively from about 0.05% to about 0.4%, by weight, alternatively from about 0.1% to about 0.2%, by weight, based on the weight of the composition.

The anti-aging composition may include any number of appropriate surfactants as additives. Appropriate surfactants for the anti-aging composition may include, but are not limited to, glyceryl stearate, myristic acid, palmitic acid, stearic acid, polyethylene glycol (PEG)-100 stearate, PEG-60 hydrogenated castor oil, seareth-100, or combinations thereof. The total amount of the surfactants may be any appropriate amount, such as, for example, about 2% or less, about 1% or less, alternatively from about 0.2% to about 1%, alternatively from about 0.3% to about 0.5%, by weight, based on the weight of the composition.

The anti-aging composition may include any number of appropriate non-water solvents as additives. Appropriate non-water solvents for the anti-aging composition may include, but are not limited to, denatured alcohol, caprylyl glycol, glycerin, 1,2-hexanediol, methylpropanediol, or combinations thereof. The total amount of the non-water solvents may be any appropriate amount, such as, for example, about 20% or less, alternatively from about 10% to about 20%, alternatively from about 13% to about 17.5%, by weight, based on the weight of the composition.

The anti-aging composition may include any number of other appropriate additives or adjuvants. Representative additives and adjuvants include, for example, water-soluble or water-miscible solvents or co-solvents, dispersion enhancing agents, moisturizers, colorants, fillers, antioxidants (e.g., EDTA, butylated hydroxytoluene (BHT), and tocopherol), essential oils, fragrances, dyes, neutralizing or pH-adjusting agents (e.g., citric acid, triethylamine (TEA), and sodium hydroxide), conditioning or softening agents (e.g., panthenol and allantoin) and extracts, such as botanical extracts. Additives and adjuvants may be present in the compositions in amounts generally ranging from about 0.01% to about 10%, by weight. Examples of anti-aging active agents or dermatological active agents include sunscreen agents (e.g., inorganic sunscreen agents, such as titanium dioxide and zinc oxide and organic sunscreen agents, such as octocrylene, ethylhexyl methoxycinnamate, and avobenzone), free-radical scavengers, keratolytic agents, vitamins (e.g., Vitamin E and derivatives thereof), anti-elastase and anti-collagenase agents, peptides, fatty acid derivatives, steroids, trace elements, extracts of algae and of planktons, enzymes and coenzymes, flavonoids and ceramides, hydroxy acids and mixtures thereof, and enhancing agents.

In some embodiments, an anti-aging product reduces the number and/or severity of lines and/or wrinkles in the skin. For example, regarding the percent change in wrinkles from a time point immediately after a first application, the composition after application three times a week for about 30 minutes per application, provides wrinkle reduction of one or more of the wrinkle features selected from crow's feet, forehead, labellar, nasolabial, marionette as compared to a baseline, of about 2-5% at one week, of about 5-30% at four weeks, and of about 25-45% at eight weeks, as shown in Table 2 below. For example, regarding the percent change in wrinkles from a baseline time point, the composition after application three times a week for about 30 minutes per application, provides wrinkle reduction of one or more of the wrinkle features selected from crow's feet, forehead, labellar, nasolabial, marionette as compared to a baseline, of about 5-20% immediately after a first application, of about 10-25% at one week, of about 20-40% at four weeks, and of about 30-50% at eight weeks, as shown in Table 3 below.

Raw Materials

Compositions as described in the representative embodiments according to the disclosure, and compositions as exemplified herein include raw materials selected from commercially available materials.

Examples

The invention is further described in the context of the following examples, which are presented by way of illustration, not of limitation. The inventive compositions may be used alone as an anti-aging product, such as, for example, a serum, a lotion, a liquid, a cream, a gel, an emulsion, a primer, or a BB cream, or loaded into a skin mask patch, such as, for example, a hydrogel skin mask patch or a biocellulose skin mask patch.

Compositions

Two inventive compositions were formed that included an anti-aging composition including hyaluronic acid, at least one anti-aging peptide, at least one skin penetration enhancer and/or at least one tensing polymer, and water. Table 1 lists the ingredients and their amounts in weight percentage in Inventive Example 1 and Inventive Example 2.

TABLE 1

Inventive Compositions

| INGREDIENT | INVENTIVE 1 | INVENTIVE 2 |
|---|---|---|
| ACETYL HEXAPEPTIDE-8 | | 0.0015 |
| ACETYL TETRAPEPTIDE-9 | 0.00345 | |
| ADENOSINE | | 0.04 |
| ALLANTOIN | 0.1 | 0.1 |
| BIFIDA FERMENT LYSATE | 10.846 | 10.846 |
| CALCIUM LACTATE | 0.9 | 1.05 |
| DIPOTASSIUM GLYCYRRHIZATE | 0.1 | 0.1 |
| DISODIUM ETHYLENEDIAMINETETRA-ACETIC ACID | 0.01485 | |
| POTASSIUM HYDROXIDE | 0.0045 | 0.0045 |
| HYDROLYZED HYALURONIC ACID | 0.1 | |
| SODIUM HYALURONATE | | 0.1 |
| TRISODIUM ETHYLENEDIAMINE DISUCCINATE | | 0.037 |
| TITANIUM DIOXIDE | 0.2 | 0.2 |
| OLEIC ACID | 0.15 | 0.15 |
| CARRAGEENAN | 3.475 | 3.8 |
| POTASSIUM CHLORIDE | 0.225 | 0.25 |
| CERATONIA SILIQUA (CAROB) GUM | 0.792 | 0.88 |
| SUCROSE | 0.108 | 0.12 |
| PULLULAN | 2 | 1.75 |
| XANTHAN GUM | 0.6 | 0.5 |
| PHENOXYETHANOL | 0.121 | 0.121 |
| SODIUM BENZOATE | 0.033 | 0.033 |
| PEG-60 HYDROGENATED CASTOR OIL | 0.4 | 0.4 |
| PANTHENOL | 0.1 | 0.1 |
| 1,2-HEXANEDIOL | 2 | 2 |
| CAPRYLYL GLYCOL | | 0.015 |
| GLYCERIN | 7.4 | 5 |
| METHYLPROPANEDIOL | 6.986 | 6.986 |
| WATER | 63.3412 | 65.416 |

Testing Results

Inventive Example 2 was tested on facial lines at five different facial locations to evaluate the anti-line efficacy of the anti-aging composition at different time points over an 8-week course of the study. The results, quantified based on clinical grading by an expert, are shown in Table 2 and Table 3.

Test subjects included Caucasian women between the ages of 25 and 55 of all skin types with skin concerns related to anti-aging (lines). The women initially had a light-to-moderate severity of lines (2-4 on a 10-point scale) as evaluated by clinical grading by an expert and separately based on a self-assessment by questionnaire.

At least two attributes (crow's feet, forehead, glabellar, nasolabial, and marionette lines) were included for each test subject, with the number of test subjects for each attribute being indicated in Table 2 and Table 3. The test subjects did not change use of their routine products during the study. Each treatment lasted 30 minutes and included 8 patches on line areas, and the treatments were performed three times per weeks. The lines of each test subject were evaluated by an expert at the beginning of the study ($T_{imm}$), immediately after the first treatment ($T_0$), after the third treatment ($T_{1w}$), after the twelfth treatment ($T_{4w}$), and after the twenty-fourth treatment ($T_{8w}$).

TABLE 2

Mean and Percent Change in Wrinkles from IMM Timepoint w/Inventive Example 2

| | $T_{imm}$ | $T_{1w} - T_{imm}$ | $T_{4w} - T_{imm}$ | $T_{8w} - T_{imm}$ |
|---|---|---|---|---|
| Crow's Feet Area (n = 51) | 2.25 ± 0.83 | −0.16 ± 0.80 (−2.25%) NS | −0.36 ± 0.78 (−12.99%) S | −0.78 ± 0.69 (−35.82%) S |
| Forehead Area (n = 43) | 2.17 ± 0.92 | −0.21 ± 0.64 (−3.53%) NS | −0.34 ± 0.76 (−7.69%) S | −0.67 ± 0.71 (−27.38%) S |
| Glabellar Area (n = 38) | 2.24 ± 0.91 | −0.07 ± 0.59 (−3.55%) NS | −0.55 ± 0.60 (−27.81%) S | −0.88 ± 0.47 (−42.35%) S |
| Nasolabial Area (n = 48) | 2.77 ± 0.76 | −0.18 ± 0.63 (−2.83%) NS | −0.43 ± 0.70 (−12.98%) S | −0.76 ± 0.60 (−27.38%) S |
| Marionette Lines (n = 39) | 2.40 ± 0.87 | −0.17 ± 0.77 (−3.95%) NS | −0.47 ± 0.82 (−17.13%) S | −0.91 ± 0.66 (−38.62%) S |

Table 2 shows the clinical grading of the facial lines and standard deviations immediately after the first treatment and the value and percentage changes in facial lines after one week, after four weeks, and after eight weeks using the composition represented as Inventive Example 2. The mean clinical grading decreased from the previous value for each datapoint, indicating that the anti-aging composition provided a progressive improvement. Although the improvements at one week were not statistically significant (NS), the improvements at four weeks and eight weeks were statistically significant (S).

TABLE 3

Mean & Percent Change in Wrinkles from Baseline Timepoint w/Inventive Example 2

| | $T_0$ | $T_{imm} - T_0$ | $T_{1\,w} - T_0$ | $T_{4\,w} - T_0$ | $T_{8\,w} - T_0$ |
|---|---|---|---|---|---|
| Crow's Feet Area (n = 51) | 2.79 ± 0.74 | −0.54 ± 0.60 (−19.3%) S | −0.70 ± 0.59 (−24.91%) S | −0.87 ± 0.65 (−32.28%) S | −1.32 ± 0.63 (−47.37%) S |
| Forehead Area (n = 43) | 2.73 ± 0.69 | −0.56 ± 0.65 (−20.43%) S | −0.77 ± 0.71 (−28.09%) S | −0.85 ± 0.65 (−32.77%) S | −1.23 ± 0.63 (−45.11%) S |
| Glabellar Area (n = 38) | 2.74 ± 0.69 | −0.50 ± 0.51 (−18.27%) S | −0.57 ± 0.55 (−20.67%) S | −1.00 ± 0.63 (−38.46%) S | −1.38 ± 0.47 (−50.48%) S |
| Nasolabial Area (n = 48) | 2.98 ± 0.69 | −0.21 ± 0.55 (−6.99%) S | −0.39 ± 0.59 (−12.94%) S | −0.61 ± 0.68 (−21.33%) S | −0.97 ± 0.68 (−32.52%) S |
| Marionette Lines (n = 39) | 2.87 ± 0.80 | −0.47 ± 0.75 (−16.52%) S | −0.64 ± 0.66 (−22.32%) S | −0.91 ± 0.87 (−33.04%) S | −1.38 ± 0.81 (−48.21%) S |

Table 3 shows the clinical grading of the facial lines and standard deviations prior to any treatment with the anti-aging composition and the value and percentage changes in facial lines immediately after one treatment, after one week, after four weeks, and after eight weeks. The mean clinical grading decreased from the previous value for each datapoint, indicating that the anti-aging composition provided a progressive improvement. All of the improvements shown in Table 3 were statistically significant (S).

The articles "a" and "an", as used herein, mean one or more when applied to any feature in embodiments of the present invention described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"One or more", as used herein, means at least one, and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed invention. All materials and methods described herein that embody the present invention can, in alternate embodiments, be more specifically defined by any of the transitional terms "comprising," "consisting essentially of," and "consisting of."

Other than in the operating examples, or where otherwise indicated, all numbers expressing quantities of ingredients and/or reaction conditions are to be understood as being modified in all instances by the term "about", meaning within 10% of the indicated number (e.g. "about 10%" means 9% to 11% and "about 2%" means 1.8% to 2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used, and may or may not reflect the final percentage of the active, wherein the final percentage of the active is dependent on the weight percent of active in the raw material.

All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. All numbers, amounts, ranges, etc., are intended to be modified by the term "about," whether or not so expressly stated. Similarly, a range given of "about 1% to 10%" is intended to have the term "about" modifying both the 1% and the 10% endpoints. Further, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

While the invention has been described with reference to a preferred embodiment, it will be understood by those skilled in the art that various changes may be made, and equivalents may be substituted for elements thereof without departing from the scope of the invention. In addition, many modifications may be made to adapt a particular situation or material to the teachings of the invention without departing from the essential scope thereof. Therefore, it is intended that the invention is not limited to the particular embodiment disclosed as the best mode contemplated for carrying out this invention, but that the invention will include all embodiments falling within the scope of the appended claims.

What is claimed is:

1. An anti-aging composition, comprising:
   hyaluronic acid;
   at least one anti-aging peptide selected from the group consisting of one or more acetyl hexapeptides, one or more acetyl tetrapeptides, and combinations thereof;
   at least one tensing polymer selected from the group consisting of pullulan, polyvinylpyrrolidone, and a combination thereof;
   an effective amount of at least one skin penetration enhancer selected from the group consisting of oleic acid, capric acid, lauric acid, myristic acid, palmitic acid, stearic acid, palmitoleic acid, linoleic acid, linolenic acid, lignoceric acid, resinoleic acid, arachidonic acid, and combinations thereof; and
   water,
   wherein the anti-aging composition is free of peptides other than the at least one anti-aging peptide,
   wherein the anti-aging composition is free of gellan,
   wherein the anti-aging composition is free of algae extracts other than carrageenan, and
   wherein the anti-aging composition is free of botanical extracts.

2. The anti-aging composition according to claim 1, wherein the hyaluronic acid comprises hydrolyzed hyaluronic acid.

3. The anti-aging composition of claim 1, wherein the at least one anti-aging peptide is selected from the group consisting of acetyl hexapeptide-8, acetyl tetrapeptide-9, and a combination thereof.

4. The anti-aging composition of claim 1, wherein the at least one anti-aging peptide is present in an amount in the range of 0.001% to 0.005%, by weight, based on the total weight of the anti-aging composition.

5. The anti-aging composition according to claim 1, wherein the at least one skin penetration enhancer comprises oleic acid.

6. The anti-aging composition according to claim 1 further comprising adenosine.

7. The anti-aging composition according to claim 1, wherein the anti-aging composition is a liquid.

8. The anti-aging composition of claim 7, wherein the at least one tensing polymer is present in an amount in the range of 1% to 3%, by weight, based on the total weight of the anti-aging composition.

9. The anti-aging composition of claim 1, wherein the water is present in an amount of at least 30% by weight of the anti-aging composition.

10. An anti-aging product, comprising:
    a skin mask patch; and
    an anti-aging composition loaded into the skin mask patch, the anti-aging composition comprising:
    hyaluronic acid;
    at least one anti-aging peptide selected from the group consisting of one or more acetyl hexapeptides, one or more acetyl tetrapeptides, and combinations thereof;
    at least one tensing polymer selected from the group consisting of pullulan, polyvinylpyrrolidone, and a combination thereof;
    at least one skin penetration enhancer selected from the group consisting of oleic acid, capric acid, lauric acid, myristic acid, palmitic acid, stearic acid, palmitoleic acid, linoleic acid, linolenic acid, lignoceric acid, resinoleic acid, arachidonic acid, and combinations thereof; and
    water,
    wherein the anti-aging composition is free of peptides other than the at least one anti-aging peptide,
    wherein the anti-aging composition is free of algae extracts other than carrageenan, and
    wherein the anti-aging composition is free of botanical extracts.

11. The anti-aging product of claim 10, wherein the skin mask patch comprises a hydrogel and the anti-aging composition is loaded into the hydrogel of the skin mask patch.

12. The anti-aging product of claim 10, wherein the skin mask patch comprises biocellulose and the anti-aging composition is loaded into the biocellulose of the skin mask patch.

13. The anti-aging product of claim 10, wherein the mask patch is triangular.

14. The anti-aging product of claim 10, wherein the hyaluronic acid, the at least one anti-aging peptide, and the at least one tensing polymer are provided in amounts sufficient to provide a reduction in an appearance of wrinkles within a month after application of the anti-aging product to skin for 30 minutes three times per a week.

15. A method of forming an anti-aging product, the method comprising:
    forming an anti-aging composition; and
    loading the anti-aging composition into a skin mask patch to form the anti-aging product;
    wherein the anti-aging composition comprises:
    hyaluronic acid;
    at least one anti-aging peptide selected from the group consisting of one or more acetyl hexapeptides, one or more acetyl tetrapeptides, and combinations thereof;
    at least one tensing polymer selected from the group consisting of pullulan, polyvinylpyrrolidone, and a combination thereof; and
    water,
    wherein the anti-aging composition is free of peptides other than the at least one anti-aging peptide,
    wherein the anti-aging composition is free of algae extracts other than carrageenan, and
    wherein the anti-aging composition is free of botanical extracts.

16. The method of claim 15 further comprising forming the skin mask patch into a triangular shape.

17. The method of claim 15, wherein the anti-aging composition provides wrinkle reduction of one or more of skin wrinkle features selected from the group consisting of crow's feet, forehead, labellar, nasolabial, and marionette lines, of about 20-40% at four weeks after application three times a week for 30 minutes per application from a baseline value.

18. The method of claim 15, wherein the anti-aging composition of claim 15 further comprises at least one skin penetration enhancer selected from the group consisting of oleic acid, capric acid, lauric acid, myristic acid, palmitic acid, stearic acid, palmitoleic acid, linoleic acid, linolenic acid, lignoceric acid, resinoleic acid, arachidonic acid, and combinations thereof.

19. The anti-aging composition according to claim 1 further comprising at least one humectant.

* * * * *